United States Patent [19]

McFarlane

[11] Patent Number: 4,750,877
[45] Date of Patent: Jun. 14, 1988

[54] INJECTION MOLDING OF A THIN-WALLED ELONGATED TUBULAR PRODUCT SUCH AS A CATHETER

[75] Inventor: Richard H. McFarlane, Geneva, Ill.

[73] Assignee: Taut, Inc., Geneva, Ill.

[21] Appl. No.: 911,413

[22] Filed: Sep. 25, 1986

Related U.S. Application Data

[60] Continuation-in-part of Ser. No. 496,979, May 23, 1983, which is a division of Ser. No. 302,490, Sep. 16, 1981, abandoned.

[51] Int. Cl.⁴ .............................................. B29B 11/06
[52] U.S. Cl. .................................... 425/573; 425/577; 425/812; 249/125
[58] Field of Search ............... 249/122, 124, 125, 142; 425/142, 144, 146–149, 151, 573, 577, 812

[56] References Cited

U.S. PATENT DOCUMENTS

| | | | |
|---|---|---|---|
| 3,385,553 | 5/1968 | Braun | 425/577 X |
| 3,807,925 | 4/1974 | Lohmann | 425/564 X |
| 4,094,660 | 6/1978 | Ilk | 249/125 X |
| 4,126,291 | 11/1978 | Gilbert et al. | 425/812 X |

FOREIGN PATENT DOCUMENTS 0413558  8/1910  France ................................ 249/142

Primary Examiner—Charles Hart
Attorney, Agent, or Firm—John Cyril Malloy

[57] ABSTRACT

The injection molding of an elongated thin-walled tubular product such as a medical catheter is accomplished through the mounting of an elongated core pin on the interior of an elongated mold cavity wherein tension is continuously applied to the core pin for the purpose of maintaining it in a predetermined, substantially centered relation to the mold cavity and further maintaining a straight line configuration of the core pin along its length. The plastic material from which the product is formed is introduced into the mold cavity while at the same time overcoming any imbalance in the flow of the plastic melt into the mold cavity and as it travels in surrounding relation to the core pin and along its length by adjusting the position of the core pin relative to the inner surface of the mold cavity.

12 Claims, 5 Drawing Sheets

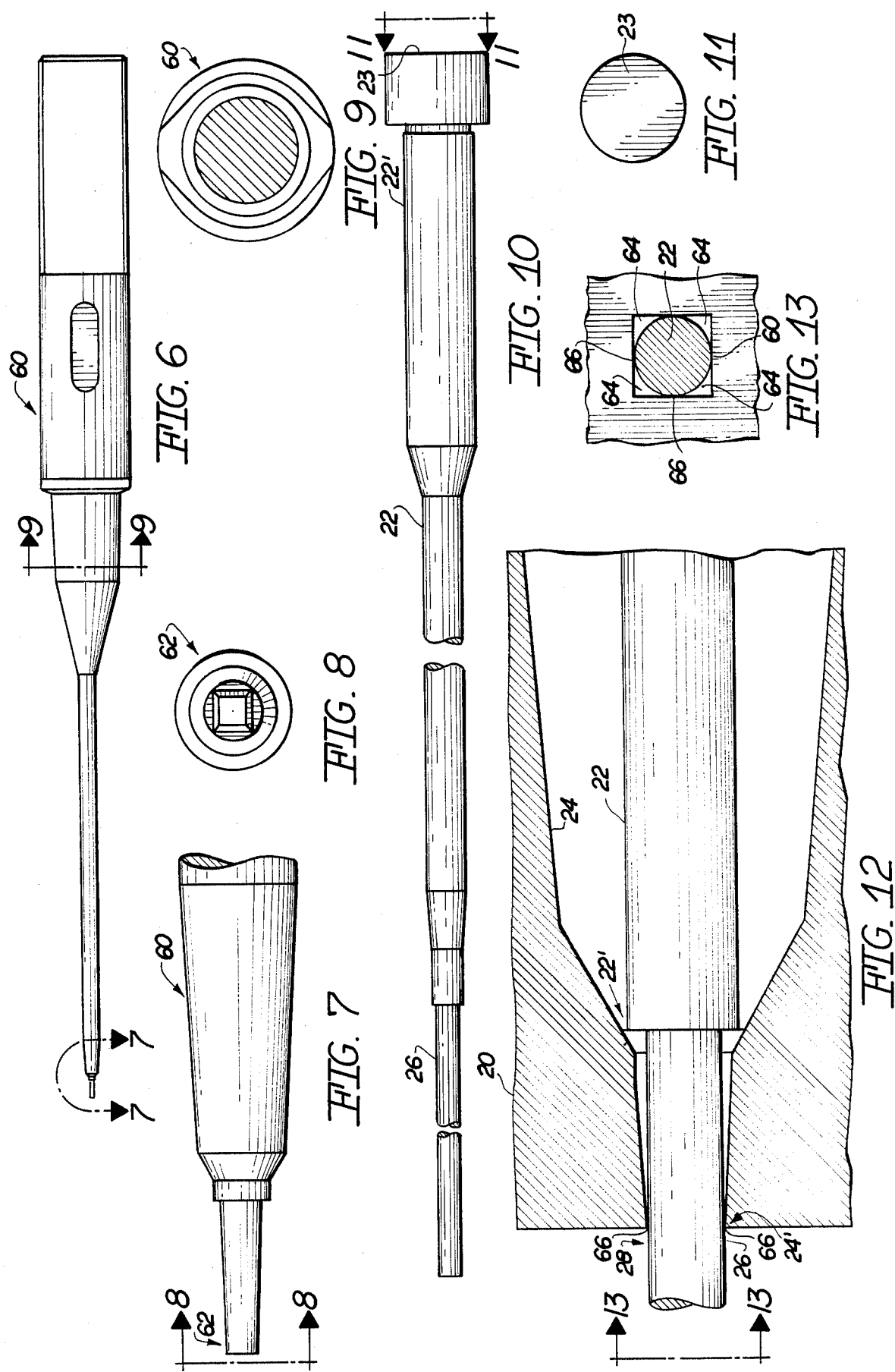

INJECTION MOLDING OF A THIN-WALLED ELONGATED TUBULAR PRODUCT SUCH AS A CATHETER

BACKGROUND OF THE INVENTION

This is a continuation-in-part application of copending patent application Ser. No. 496,979 filed May 23, 1983 which is a divisional application of then copending patent application Ser. No. 302,490 filed Sept. 16, 1981 and now abandoned.

1. Field of the Invention

An apparatus and method for accomplishing the formation of an elongated thin-walled tubular product such as but expressly not limited to a medical catheter wherein an extremely small diameter bore is maintained along with a thin wall of substantially consistent dimension throughout a majority of the length of the tubular product utilizing an injection molding technique and forcing a flow of melt into a mold cavity in surrounding relation to a central core pin itself maintained in a substantially centered relation to the mold cavity through the application of tension being applied thereto.

2. Description of the Prior Art

There is a need in the art of molding plastic products to be able to mold a plastic part having a relatively small diameter hole extending therethrough. An example of such a product is a medical catheter comprising a jacket or sleeve of plastic material through which a needle is to be inserted. Especially in the field of medical products, it is important to exert great care in maintaining the constant diameter of the central hole extending through a catheter product since this has the effect of maintaining a substantially straight shank in the finished tubular product. Also, the product must be constructed to have a consistent flex pattern and avoid "kinking" when bent or flexed. There are of course numerous other situations in which a relatively fine, small diameter hole is required to be formed through a tubular plastic molded part whether the hole is substantially coaxial with the part or not, or whether the part is cylindrical or not. Generally, the term "tubular" as used herein refers to parts which have at least one fine hole therethrough. Oftentimes, such molded plastic parts are required to have a thin wall of necessarily constant thickness with a longitudinally extending channel, having an exceptionally small diameter extending therethrough.

Previously, especially in the art of injection molding, when plastic is melted, and forced to flow into a cavity about a fine, small diameter core, the pressure of injection forcing the melt into the mold cavity if not adequately balanced during the molding operation tends to cause the thin diameter core to be displaced from its substantially centered, straight line configuration relative to the central axis of the mold cavity. This displacement is of course undesirable since a straight line configuration of the central hole as well as the shank portion of the product is required. Such displacement of the core pin relative to the interior surface of the mold cavity is also frequently caused by what may be considered an imbalance in the flow characteristics of the hot melt as it enters the mold cavity and passes along the length thereof in substantially surrounding relation to the core pin. Such imbalance may be caused by a number of factors but also has the tendency to cause uneven forces to be exerted on the core pin tending to cause its displacement from the aforementioned and preferred straight line configuration. For these reasons, the prior art has generally been limited to relatively short tubular lengths in relation to the diameter of the hole through it. If, for example, the tubular product is to be relatively long, which is quite common in the medical industry, a small hole, especially a hole in a thin walled tube is extremely difficult to make with any great degree of accuracy. In addition, different materials provide different problems.

In manufacturing the type of product set forth above, it is often required to make small diameter holes of about 0.020 inches in a tubular product of plastic having a longitudinal dimension of an inch or more with an outside diameter of approximately 0.032 inches. It is readily apparent therefore that the wall of such a tubular product is extremely thin and in the range of about 0.006 inch in thickness. Oftentimes it is desired that the hole or passageway through the molded plastic part be in the range of 0.002 inches to about 0.100 inch in diameter.

Accordingly, in the formation of the type products referred to above, a primary difficulty has been that the core pin must be of an extremely small diameter and therefore subject to pressures of the inflowing melt forced into the mold cavity utilizing injection molding techniques. The pressure or force of the incoming melt has a tendency to exert a force on the very thin core pin resulting in a displacement from its straight line configuration within the mold cavity and the production of a deffective thin walled tubular product.

Another problem generally associated with the injection molding technique of products of the type referred to herein is the breakdown in the intensity of the plastic material utilized to form the tubular product when the material is forced to travel along what may be referred to as a circuitous path from the point of leaving the injection nozzle to the point of entering and passing along the length of the mold cavity. This is particularly true when the plastic material, after being melted, is forced to travel along a circuitous path or a path including one or more right angles at a relatively high speed. Attempts to slow the speed of injection of the inflowing melt however has met with little success especially in the formation of thin walled tubular products. This is primarily due to the fact that the melt rapidly cools and therefore hardens as it travels along the length of the mold cavity especially at slow speeds. Accordingly, when using injection molding techniques at such slow speeds, attempts have been made to raise the temperature of the plastic material to a somewhat higher than normal temperature, prior to injection to overcome the problems of the prior art. This higher temperature results in a degradation of many plastic materials which has obvious disadvantages in the making of thin walled tubular products.

As set forth above, various materials utilized in the formation of thin walled tubular products present specific problems when utilizing conventional injection molding techniques. The referred to plastic material Teflon cannot be used in injection molding incorporating circuitous paths under high speed conditions. To the contrary, the injection molding of Teflon along right turn paths or circuitous paths require a slow injection speed. However, it is recognized that in the formation of thin walled tubular products, high speed injection is necessary to accomplish filling of the mold cavity before cooling of the melt.

Other prior art techniques and apparatus for the formation of relatively long, thin walled tubular products include the use of drilling with an extremely fine drill or a laser beam. Hhowever, such techniques seriously limit the length of the tube which may be created. Also, it is of course well known to extrude a tube and draw the tubular product to a smaller diameter. This technique however presents limitation as to the configuration of the tube wall and the latter type product is limited to a hole or external configuration which is cylindrical. Generally, such prior art extrusion techniques would not be practical when it is desired to produce such products with a multi-stepped wall configuration such as when a hub or angeled wall tip is desired on the product.

Accordingly, there is a need in the industry for an apparatus and method of producing elongated thin walled tubular products such as, but expressly not limited to, medical catheter type products, preferably using an injection molding technique in a manner which will overcome problems associated with the displacement of a relatively fine core pin relative to its preferred coaxial positioning in the mold cavity in which the tubular product is formed.

SUMMARY OF THE INVENTION

The present invention relates to a molding assembly and attendant method for the formation of an elongated, thin walled tubular product from a moldable plastic material wherein the tubular product is specifically designed to have a substantially consistently dimensioned wall thickness throughout its length and further characterized by the diameter of the central bore or channel extending through the tubular product being of extremely small transverse dimension. Throughout the description of the invention provided herein, reference will be made to a tubular product such as a medical catheter structure. However, it is herein emphasized that the molding assembly and method utilized in the formation of the subject tubular product is not limited to catheter devices but rather a variety of tubular products having the structural characteristics as set forth above.

The molding assembly of the present invention incorporates an injection molding technique characterized by the introduction of plastic material in heated and melted form, herein referred to as melt, being forced into an elongated mold cavity, in at least one embodiment, in a direction which is in-line or coaxial to the length of the mold cavity. Such in-line injection molding is conducted at least in part for the purpose of avoiding a circuitous or right angled path of travel of the melt as it travels from the injection nozzle, into and throughout the length of the mold cavity. However, it should be strongly emphasized that while the subject invention is described in detail specifically with reward to an in-line injection molding apparatus and technique, the present invention further contemplates that the in-line injection referred to herein could be other than a pure coaxial introduction of the hot melt into the mold cavity and an initial introduction of the hot melt from a transverse or perpendicular direction to the length of the mold cavity in core pin is included in the concept of the present invention.

A core pin is mounted to extend in depending relation on the interior of the mold cavity and is substantially centrally disposed so as to be oriented and maintained in the mold cavity. It is an important feature of the present invention to maintain the core pin in a substantially centered and straight line orientation relative to the mold cavity and prevent displacement thereof due to the forces exerted on the core pin because of the inflowing melt entering the mold cavity in surrounding relation to the core pin.

The maintenance of the core pin in the aforementioned substantially centered position and straight line configuration insures that the resulting tubular product will have a straight, substantially centered channel and a shank portion of the tubular product being also substantially straight. However, as used herein, it is emphasized that the wall configuration of the tubular product may in fact be stepped or include a hub portion, etc. and still come within the meaning of straight or straight-line configuration.

An important feature of the present invention is the application and maintenance of a tensioning force applied to an exterior portion of the core pin which extends from a distal end of the mold cavity. Tension or force is applied to the exterior portion of the core pin in a direction which is coaxial to the length of the core pin. In addition, the opposite or what may be considered proximal end of the core pin is adjustable secured relative to the mold cavity. Such adjustable connection allows for the final adjustment or orientation of the core pin to overcome any imbalance in the flow of melt as it enters and travels along the length of the cavity. Even with the existence of axial tension on the core pin, such imbalance flow of melt will tend to displace it.

In order to further facilitate maintenance of the core pin in the required straight line position within the mold cavity, the present invention includes the provision of a distribution means mounted substantially adjacent to and in fluid communication with the open end or entrance of the mold cavity. The distribution means directly receives the melt substantially as it exits the injection nozzle. The distribution means is specifically structured to control the entry of the melt into the open end or entrance to the mold cavity in a substantially equally distributed manner such that the melt surrounds the core pin both upon entrance and travel of the melt throughout the length of the mold cavity. Such distribution is accomplished through the provision of what may be referred to as a spider element having an array of apertures surrounding an extended axis of the core pin and defining fluid communication between the melt as it exits the injection nozzle and the entrance or open end of the mold cavity.

Further, the spider element is structured to engage and supportingly position the core pin in depending relation to the interior of the mold cavity. Adjustment means may be attached or used in combination with the spider element so as to minimaly vary its position and accordingly the position of the core pin so as to insure an accurate, preferred position thereof within the mold cavity. It is to be emphasized that the adjustment of the spider element and accordingly the core pin may be extremely small to overcome any imbalance in the flow of melt entering the mold cavity in traveling along its length. Accordingly, the core pin may be removed from a true coaxial relation to the mold cavity but such minimal variance from such a coaxial disposition will not derrogatorily affect the wall thickness of the tubular product even though the core pin may no longer be in a true centered position relative to the mold cavity.

Other features of the present invention include the provision of a vent means located at a distal end of the core pin and mold cavity which is defined by a plurality of spaces formed by the incongruent peripheral configuration of the mold cavity and an exiting portion of the core pin. The spaces are specifically dimensioned to allow the escape of air from the mold cavity concurrently to the entry and travel of the melt into and along the length of the mold cavity towards the distal end thereof. Accordingly, the resulting formed tubular product is absent any flashing at the extremity thereof formed at the site of the core pin and mold cavity defining the vent means.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature of the present invention, reference should be had to the following detailed description taken in connection with the accompanying drawings in which:

FIG. 6 is a longitudinal side view of a mandrel struture from which the mold cavity of the present invention is formed.

FIG. 7 is a detailed view in partial cutaway along line 7—7 of FIG. 6.

FIG. 8 is an end view along line 8—8 of FIG. 7.

FIG. 9 is a sectional view along line 9—9 of FIG. 6.

FIG. 10 is a longitudinal side view in partial cutaway of the core pin of the present invention.

FIG. 11 is an end view along line 11—11 of FIG. 10.

FIG. 12 is a detailed view in partial section and cutaway showing relative positioning of the core pin and mold cavity so as to define a vent structure of air exiting the mold cavity.

FIG. 13 is an end view along line 13—13 of FIG. 12.

Like reference numerals refer to like parts throughout the several views of the drawings.

DETAILED DESCRIPTION OF THE PREFERRED EMBODIMENT

Figure 1:
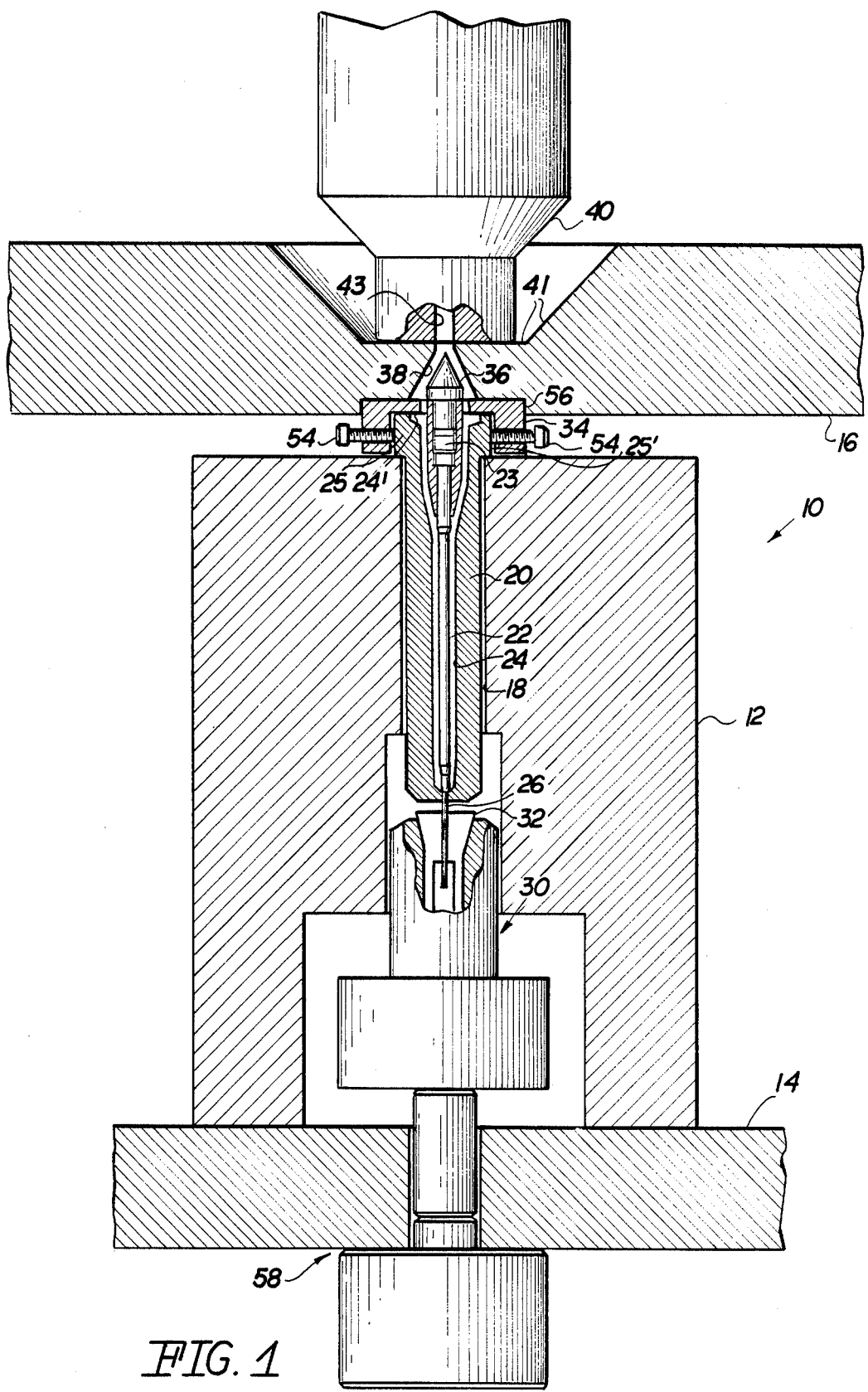
FIG. 1 is a detailed view in section and partial cutaway showing the molding assembly of the present invention.
Figure 2:
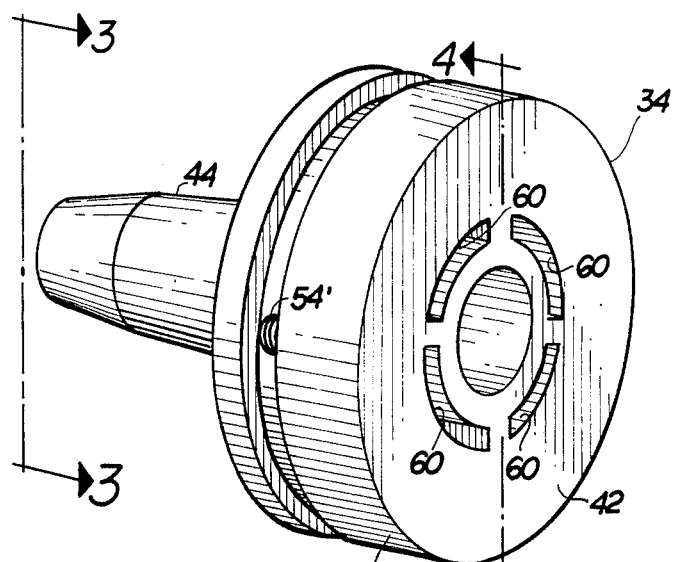
FIG. 2 is an isometric view of a component of the present invention relating to the distribution of the melt immediately prior to entering the mold cavity thereof.
Figure 3:
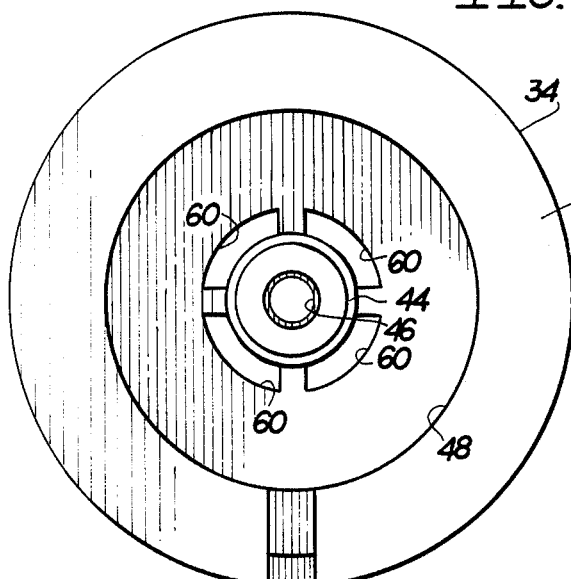
FIG. 3 is an end view along line 3—3 of FIG. 2.
Figure 4:
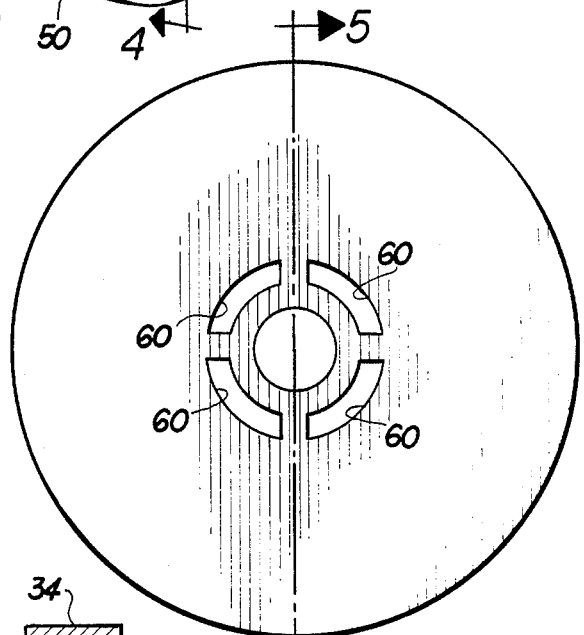
FIG. 4 is an opposite end view along line 4—4 of FIG. 2.

As shown in FIG. 1, the molding assembly of the present invention is generally indicated as 10 and may be used in combination with a commercially available injection molding press such as a 28 ton Arberg. However, it should be emphasized that in a mass production environment, the specific injection molding press apparatus may vary greatly. Accordingly, the molding assembly of the present invention includes a support member 12 positioned between a lower platen 14 and an upper platen 16. The support member 12 has a central bore 18 in which mold cavity 20 is supported. A core pin 22 is positioned and maintained within the cavity portion 24 of the mold cavity 20 in a straight line configuration.

The core pin 22 has an exterior portion 26 of sufficient length and dimension to extend outwardly from the cavity 24 to the exterior of the mold cavity 20 at a distal end thereof generally indicated as 28 in FIG. 12. The purpose of the external portion 26 protruding from the mold cavity 20 is to provide means for applying an axially applied tension to the core pin 22 by means of a tensioning means generally indicated as 58, a collect actuating means 30 and a gripping structure in the form of a collet 32.

The opposite end of the core pin 22 is supported by a spider element 34 (see FIGS. 2-5) serving as a distribution means as well as a structure for supporting the core pin 22 in supported and depending relation on the interior of the cavity 24 of mold cavity 20. In addition to the spider element 34, the distribution means also includes a deflector element 36 in the form of a deflecting pin preferably having a conical exterior configuration and positioned within orifice 38 in direct receiving relation to plastic melt issuing, under pressure, from injection nozzle 40.

Figure 5:
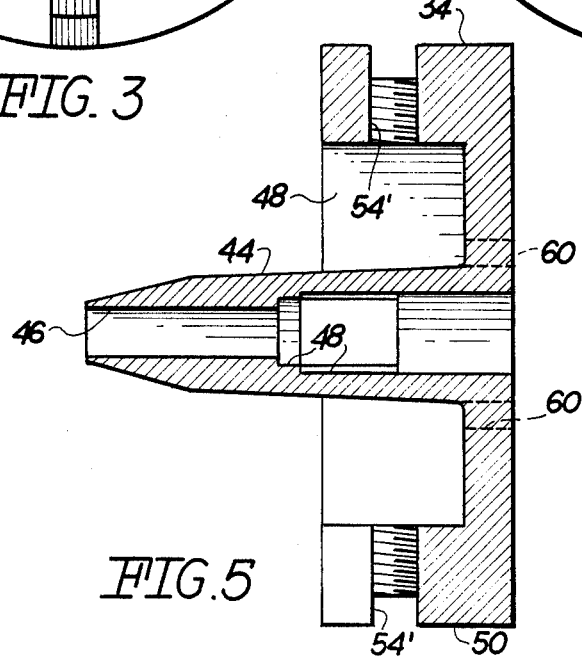
FIG. 5 is a sectional view in detail showing the interior structural features of the spider element of the embodiment of FIG. 2.

With reference to FIGS. 2 through 5, the spider element 34 defining a portion of the distribution means comprises a base portion 42 having an integrally formed and outwardly extending sleeve 44 including a central bore 46 formed therein and having a stepped configuration as at 48 along a portion of its length. The stepped configuration 48 defines a recess so as to receive and support an enlarged head portion 23 at the proximal end or extremity of the core pin 22 as best shown in FIGS. 1 and 10. In addition, a depending somewhat enlarged stem 22' of core pin 22 fits within the adjacent portion of bore 46 as shown in FIGS. 1 and 5.

Again with reference to FIGS. 2 through 5, the base 42 has a recess 48 defined in part by a depending annular flange or skirt 50 wherein the proximal, somewhat enlarged end 25 of mold cavity 20 is received within the recess 48 for positioning of the base 42 of the spider element 34 as shown in FIG. 1. A plurality of adjustable connector elements 54 are provided to adjust and maintain a preferred position of the core pin 22 relative to the cavity 24 of the mold cavity 20 to overcome any imbalance in the flow of plastic melt as it enters the cavity 24. It should further be noted that the configuration and transverse dimension or diameter of the spider base 42 is such as to fit within a counterbore 56 integrally formed in the upper platen 16.

As clearly shown in FIG. 1 and with specific references to FIGS. 2 through 5, an important feature of the present invention is the provision of a plurality of apertures or entry ports 60 integrally formed in the spider base 42 which establish fluid communication between the orifice 38 and the open end 24' of the cavity 24 of mold cavity 20. Further, the apertures or entry ports 60 are disposed in what may be considered a circular array or in a configuration which serves to surround the barrel or sleeve 44 and therefore the core pin 22 as well as the secured core pin head 23. By virtue of this configuration, the melt is first effectively deflected by the deflecting pin 36 and distributed as it passes through the entry ports 60 and into the open end 24' of the mold cavity 20 in surrounding relation to the pin 22 as well as the depending barrel 44 supporting the head 23 of the core pin 22.

With reference to FIGS. 6 through 9, a cavity mandrell is generally indicated as 60 which is provided to create the indicated interior surfaces of the cavity 24 of mold cavity 20. This is accomplished by hard nickel plating the cavity mandrel 60 to a significant thickness and subsequently removing the cavity mandrel 60 from the nickel form. Final adjustment of the final dimensions provides a specific gap (see FIGS. 12 and 13) defining the vent means to be described in detail hereinafter.

With regard to the vent means (see FIGS. 12 and 13), there is provided a plurality of spaces 64 created between points of engagement 66 as the circular peripheral cross section of the pin 22 engages the multi-sided peripheral configuration of the distal end of the mold cavity generally indicated as 24" in FIG. 12. Due to the difference in configurations between the circular core pin 22 and the multi-sided interior surface of the mold cavity, the plurality of spaces 64 are the result. It is also important to note that the spaces 64 are specifically dimensioned to allow the escape of air from the cavity 24 as the plastic melt enters the opposite or proximal end of the mold cavity and travels down the length of the mold cavity in surrounding relation to the pin 22. Flash of the hot melt beyond the core pin at the location generally indicated as 22' in FIG. 12 is prevented due to the closeness in tolerance provided at this location and also at least in part, due to the axial tension placed on the core pin 22 by the tensioning means 58 as described above. This has the effect of eliminating flashing from the resulting formed tubular product.

With regard to FIG. 1, the position shown represents the element of the subject molding assembly in a clamped position ready for injection of the plastic melt into the interior of cavity 24 of mold cavity portion 20. After molding is complete and the plastic melt has been solidified, the lower machine platen 14 moves in a downward direction in terms of the orientation of the components as shown in FIG. 1, and takes with it both the mold cavity 20 and the spider element 34 due to the fact that the gripping collet 32 is still in gripping engagement with the exterior portion 26 of core pin 22. In operation, a typical mold cycle using the mold assembly 10 of the present invention is as follows. The deflector pin 36 is not yet attached to the spider element, defining the deflecting means, as shown in the position in FIG. 1. Prior to attachment of the deflector pin 36 in the manner shown in FIG. 1, the core pin 22 is inserted into the central bore 46 of the barrel or sleeve 44 of the spider element 34. After the core pin 22 is so positioned, the deflector pin 36 is reattached and the spider element 34 is then positioned relative to the proximal end 25 of the mold cavity 20 which itself is positioned on the interior of the support member 12 (see FIG. 1).

The mold cycle is then initiated which starts the lower machine platen 14 moving upwardly so as to bring the spider element 34 into engagement with the upper stationary platen 16. Such aligned securement between the spider element 34 and the upper platen 16 is insured due to the transverse dimension of the base 42 of the spider element 34 fitting within counterbore 56 as explained above. While this occurs, the gripping collet 32 is closing around and in tight gripping engagement with the external portion 26 of core pin 22 by actuation of the collet activating means generally indicated as 30. The gripping of the external portion 26 by the gripping collet 32 and the combined operation of the collect 32, collet actuating means 30 and tensioning means 58 applies a preset amount of tension in an axial direction to the core pin 22 thereby stiffening the core pin 22 and helping it maintain a straight, linear orientation during the injection of the plastic melt into the cavity 24 of mold cavity 20.

As the mold cavity 20 and spider element 34 are moved into engagement with the upper platen 16, they are guided into alignment with the channel 38 of platen 16 by the base 42 of the spider element 34 seating within the shallow cylindrical counterbore 56. Upon completion of the movement of the lower platen 14, the mold cavity 20, spider element 34 and upper stationary platen 16 are clamped together under high pressure. When the control facilities associated with the injection press receive the signal that the clamping has been completed, the molding machine injection nozzle 40, which has been resting a short distance above the mating surface 41 formed in the upper stationary platen 16, moves into engagement with the upper machine platen 16. The plastic melt is then injected, under high pressure, from the nozzle orifice 43 into the connecting orifice 38 and into direct engagement with the deflecting pin 36. The coninally formed deflecting pin 36 directs the melt towards the injection port 60 of the spider element 34 to accomplish distribution of the plastic melt as it enters the open end 24' of the cavity 24 of mold cavity 20. The plastic melt then flows through the plurality of apertures or injection ports 60 into the mold cavity.

As set forth above, it has been found necessary to apply tension to the core pin 22, by the tensioning means 58 exerting a predetermined axially applied pressure to the exterior portion 26 and accordingly, to the remainder of the core pin 22. However, it has been determined that this alone is sometimes not sufficient to maintain the core pin 22 in the required centered relation on the interior of the cavity 24 of mold cavity 20. In certain situations such as when an imbalance or unevenness of the flow of melt into the mold cavity occurs, it has been determined that it is advantageous to also provide means to adjust and subsequently balance the flow dynamics of the plastic melt as it enters the mold cavity and travels along the length thereof and the length of the core pin. This is accomplished by adjusting the relative position of the spider element and accordingly the core pin relative to the mold cavity by means of a plurality, preferably four, adjusting connectors 54 threadedly mounted within the connecting apertures 54' of the spider element 34. Therefore, through the structure of the present invention as shown in FIG. 1, it is possible to balance and selectively distribute the flow of the polymer melt as it enters the cavity 24, through injection ports 60 so that the forces exerted on the core pin 22 do not exceed the core pin's ability to remain in the proper straight line configuration within the cavity 24 and in proper spacing from the interior surfaces of the mold cavity 24. Again, it is to be emphasized that any adjustment of the core pin relative to the central axis of the mold cavity 24 may be extremely minor. Accordingly, while the core pin may be selectively displaced from a true coaxial position relative to the mold cavity, such minor displacement will not be sufficient to alter the required straight-line configuration of the shank of the finished tubular product.

As set forth above, the vent means in the form of a plurality of spaces 64 (see FIGS. 12 and 13) allows the evacuation of air normally existing within the cavity 24 as the melt enters the open end 24' and passes down through the length of the cavity 22 in surrounding relation to the core pin 22. In actual practice, the gap or spacing between the interior surface of the mold cavity as at 24' (see FIG. 12) and the core pin as at 22' may vary from approximately 0.0002 inches to approximately 0.001 inches depending upon the particular polymer being used.

The multi-sided or square configuration as outlined in FIG. 13 serving to define, at least in part, the vent means also serves another very important function in that it provides accurate alignment of the core pin 22 relative to the interior surface of the mold cavity. This is due to the fact that the points of engagement 66 firmly contact and align the core pin 22 again as shown in FIG. 13.

Upon completion of the mold cycle, the injection nozzle 40 retracts slightly and the lower platen 14 moves downwardly taking with it the mold cavity and the spider element while still maintaining the core pin 22 under axial tension. Upon complete retraction of the lower platen 14, the tension on the core is released by retracting of the collet actuating means 30 and disengagement of the gripping collet 32 from the exterior portion 26 of the core pin 22. As the molding press opens and the mold cavity 20 and spider element 34 are removed from the upper machine platen 16, they also carry with them a solidified conically configured runner (not shown for purposes of clarity). The melt separation occurs at approximately the end of the injection nozzle 40 with the melt material remaining in the nozzle orifice 43 but removed from connecting orifice 38. The result is the formation of a conically shaped runner on deflector pin 36 which may be discarded.

Figure 14:
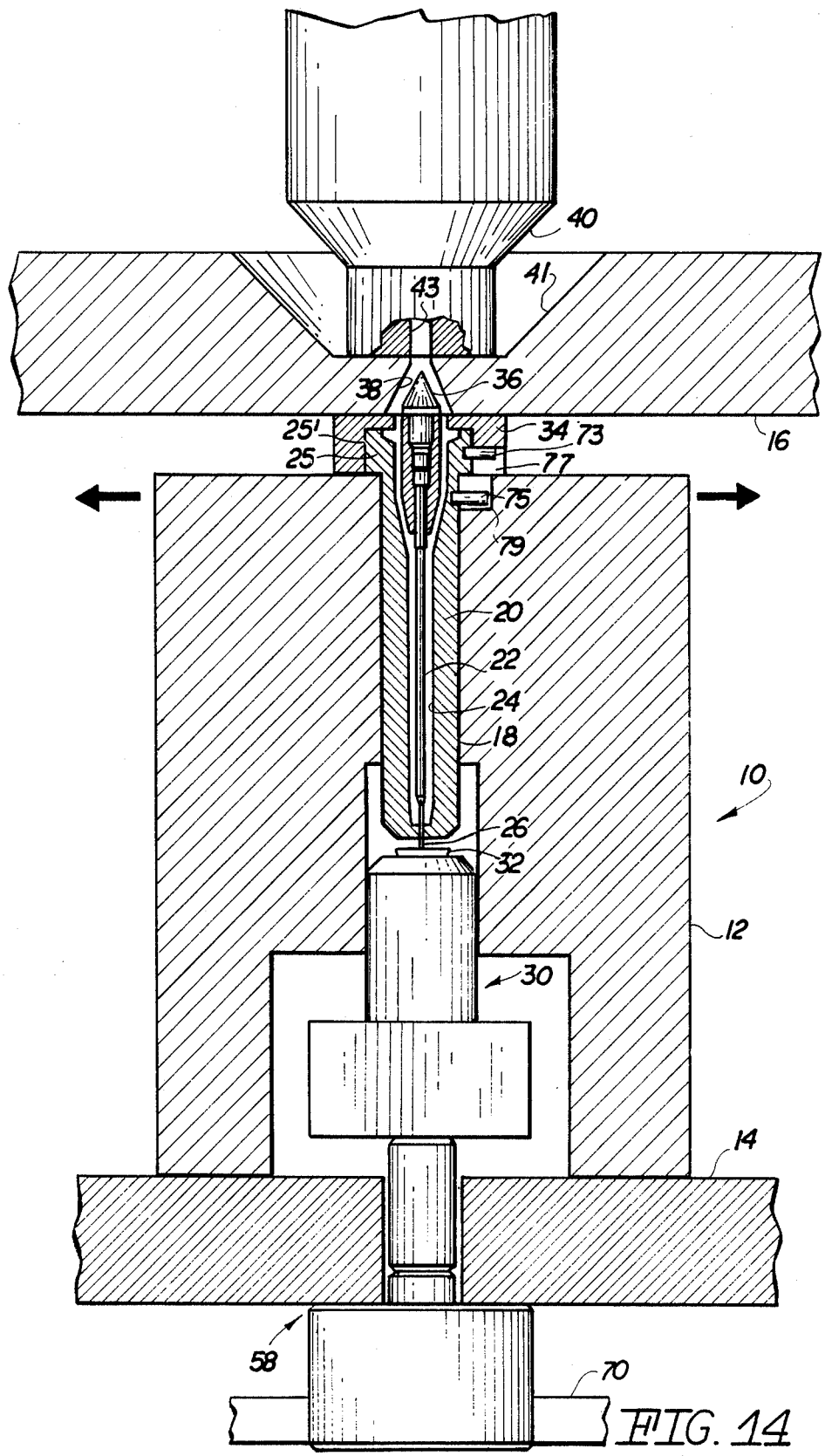
FIG. 14 is a detailed sectional view in partial cutaway of the molding assembly of the present invention used in combination with an automatic and pre-programmable adjustment assembly.
Figures 15, 16:
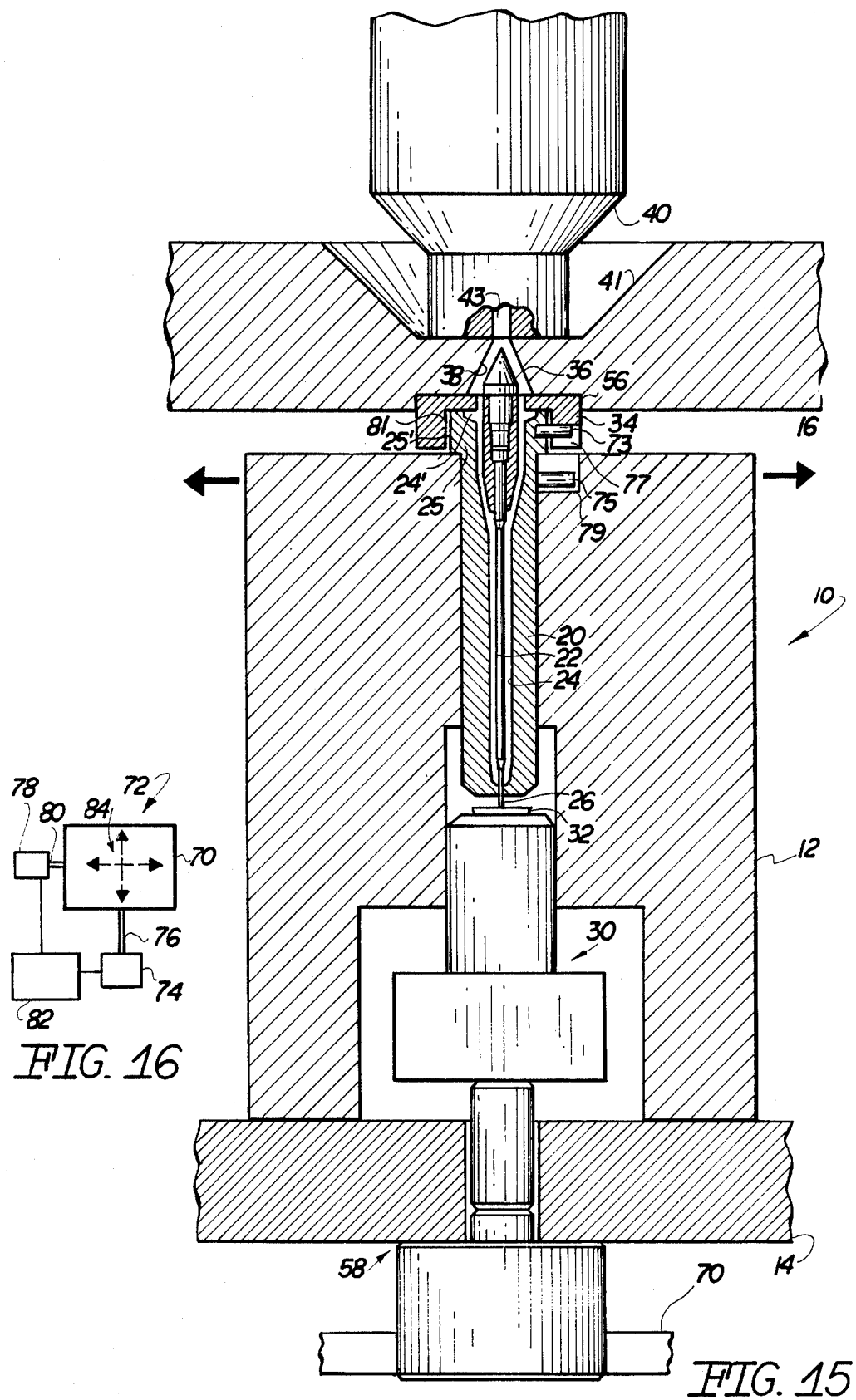
FIG. 15 is yet another embodiment of the molding assembly of the present invention also used in combination with an automatic adjustment assembly.
FIG. 16 is a schematic representation of the structural components and operative features of the automatic adjustment assembly of the present invention.

Additional embodiments of the present invention are shown in FIGS. 14, 15 and 16 wherein the molding assembly 10 of FIGS. 14 and 15 are essentially the same as the structural components outlined with regard to FIG. 1. More specifically, the molding assembly is generally indicated as 10 and may be used in combination with the aforementioned commercially available injection molding press having applicable performance characteristics. However, the particular embodiments of FIGS. 14, 15 and 16 are perhaps more adaptable for use in combination with other mass production facilities as will be pointed out in greater detail hereinafter. The embodiments of FIGS. 14 and 15 include a support member 12 positioned between the lower platen 14 and the upper platen 16. The support member 12 has a central bore 18 in which mold cavity 20 is supported and the core pin 22 is maintained under tension within the cavity portion 24 of mold cavity 20. The tensioning means 30 and collet 32 operate in the same manner with respect to gripping engagement with the protruding distal end 26 of the core pin as shown in FIGS. 14 and 15. Similarly, the collet actuating means 30 cooperates directly with the tensioning means 58 so as to apply and maintain such axial pressure specifically on the distal protruding portion 26 and generally on the core pin 22.

However, the embodiments of FIGS. 14 and 15 differ from that in structure and to some extent operation from that of FIG. 1. More specifically, the embodiment of FIG. 1 incorporates a plurality of adjustment screws 44 extending through the base 34 of the spider and into engagement with the external surface of the top of the mold cavity 24 as at 25. As set forth in detail above, the purpose of this adjustment, the manual adjustment of such pins is necessary to adjust and subsequently balance the flow dynamics of the plastic melt primarily at a location within the mold cavity downstream of the spider element 34 and along at least a portion of the length of the mold cavity 24. Accordingly, the relative position of the spider element and the core pin 22 attached thereto relative to the interior surface of the mold cavity is accomplished due to the placement and adjustable features of the plurality of adjusting screws 54.

However, in the embodiment of FIG. 14, the spider element 34 is shown in engagement with the head 25 of the mold cavity 20 eliminating any spacing therebetween as at 25'. It is again to be noted that in the embodiment of FIG. 1, a specific spacing is provided between the head or upper portion 25 of the mold cavity 20 and the interior surfaces of the spider 34 as at 25' to provide for the relative adjustment therebetween when adjustment screws 54 are in fact manipulated.

In the embodiment of FIG. 14, an automatic, pre-programmable adjustment means generally designated as 72 in FIG. 16 is provided to regulate the position of both the spider element 34 and the mold cavity 20 to which it is now fixedly attached. As shown in FIG. 14, the positioning platform 70 is associated with the entire mold assembly 10. It is to be emphasized that the placement of the adjustable platform 70 is representative only in association with the molding assembly 10 is not necessarily in the manner shown in FIG. 14 and as shown is positioned so as to drive the entire assembled components including the support member 12, lower platen 14 and combined tensioning means 58 and collet actuating means 30. It is also recognized that in actual practical application, the positioning platform 70 of the adjustment means 72 in fact will not be positioned to absorb any significant portion of the force necessarily exerted on the entire assembly 10 when lower platen 14 is clamped into position for introduction of the melt as shown in FIGS. 1, 14 and 15. Accordingly, the actual positioning in FIGS. 14 and 15 of the positioning platform 70 of the automatic adjusting means 72 is provided for purposes of explanaton and is generally considered to be representative only. In any event, the adjustment means 72 will be pre-programmed through the provision of control facilities 82 to control servo motors 74 and 78 serving to drive the positioning platform 70 in either and X and Y direction as generally represented at 84 by means of drive shaft 76 and 80. This can occur at any time prior to clamping of the molding press. The specific "flow imbalance characteristics" of a particular mold cavity 20, with regard to a specific core pin 20 with which it is always used, will be stored into a memory facility associated with the control assembly 82. The recognition by the control facility 82 of the automatic adjusting means 72 of a particular mold cavity 20 and its associated core pin 22 will serve to control the specific minor positioning adjustments, along an X-Y axis by "remembering" the pre-programmed X-Y coordinates for that particular core pin and mold cavity combination and overcome any flow imbalance characteristics associated therewith. The referred to X Y positioning or X-Y axis is to be considered in a plane perpendicular to the longitudinal axis of the core pin and/or injection nozzle 40.

Other structural features associated with the specific embodiment of FIG. 14 includes the provision of a stabilizing pins 73 and 75 which pass into open ended slots 77 and 79 respectively so as to rotationally locate the mold cavity 20 relative to spider 34 (by pin 73 and slot 77) and the mold cavity 20 with regard to the support member 12 (accomplished by pin 75 being disposed within open ended slot 79).

With regard to the embodiment of FIG. 15, the basic components of the mold assembly 10, support member 12, lower platen 14, etc. are the same with regard substantially to the embodiments 1 and 14.

In addition, the embodiment of FIG. 15 even closer resembles the embodiment of FIG. 1 and differs specifically from embodiment of FIG. 14 by providing a specific spacing in the area designated as 25' between the inner surface of the base 42 of the spider 34 and the outer surface of the head 25 of the mold cavity 20. Further, a pin member 73 is positioned into open ended slot 77 to prevent relative rotation between the mold cavity 20 and the spider 34 and similarly, the securement pin 75 being affixed or attached to mold cavity 20 is positioned within open ended slot 79 of the support member 12 for purposes of preventing relative rotation therebetween.

It should be noted that in the embodiment of FIG. 14 there is no countersunk bore 56 which appears in the embodiments of FIGS. 1 and 15. This is due to the fact that the spider 34 and head portion 25 of FIG. 14 essentially move together as a unit and both are adjustable relative to the platen 16 and distribution channels 38, as set forth above, immediately prior to the clamping or injection ready position a shown in FIG. 14.

To the contrary, however, the countersunk bore 56 appears in the lower portion of upper platen 16 so as to properly center the spider 34 upon a rise of the lower platen 14 and associated support member 12 therein. The automatic operation and adjustment capabilities of the adjustment means 72 (see FIG. 16) is programmed to occur based on the specific melt inflow imbalance characteristics associated with a particular mold cavity 20 and associated core pin 22 combination. As set forth above, such inflow imbalance characteristics of each separate mold cavity 20 and associated core pin 22 (the same mold cavity and core pin will always be used together as a unit) will be maintained in the memory of the control facility 82 of the automatic adjustment means 72. Accordingly, the servo motors 74 and 78 will be activated again by the control facility 82 of the automatic adjusting means 72 along the appropriate X Y axis in order to compensate for the aforementioned inflow imbalance characteristics. However, in the embodiment of FIG. 15, the lower platen 14, support member 12, tensioning means 58, and collet 32 and collet actuating means 30 will be movable along with the secured mold cavity, as a unit, and the mold cavity 20 will be movable relative to the spider and core pin. Hence, the provision of the space distance 25' in the embodiment of FIG. 15 between the interior surface of the base of the spider element 34 and the exterior surface of the head 25 of the mold cavity 20 exists and is necessary in order to accomplish such at least minimal adjustable movement.

It is therefore to be understood that the following claims are intended to cover all of the generic and specific features of the invention herein described, and all statements of the scope of the invention which as a matter of language, might be said to fall therebetween.

Now that the invention has been described,
What is claimed is:

1. A molding assembly designed for high speed injection of melt for molding an elongated thin-walled tubular product, said molding assembly comprising:
    (a) a mold cavity including an interior surface configured to define the exterior surface of the tubular product and positioned to receive an in-flow of melt into an open end of the mold cavity,
    (b) a core pin disposed on the interior of said mold cavity and having an elongated, straight-line configuration and being disposed within said mold cavity in spaced relation to said interior surface of said mold cavity along a major portion of its length,
    (c) a support member having a central bore and being positioned between an upper and a lower platen, said central bore being structured to receive and support said mold cavity therein,
    (d) a tensioning means mounted exteriorly of said mold cavity adjacent an end thereof opposite to said open end and attachable to an exterior portion of said core pin for placing axially applied tension thereon,
    (e) distribution means disposed adjacent said open end of said mold cavity in receiving relation to the in-flow of the injected melt and structured for distributing the melt axially in surrounding relation to the core pin,
    (f) said distribution means further comprising a spider element mounted adjacent said open end of said mold cavity and supportingly engaging said core pin, so as to be movable therewith, said spider element disposed in receiving relation to the in-flow of melt, and comprising a plurality of apertures disposed in communicating relation with the interior of said mold cavity at said open end and collectively arranged for the direction of the flow of melt about said core pin into said mold cavity,
    (g) said distribution means further comprising a deflector pin mounted on said spider element and disposed in aligned, receiving relation to the in-flow of melt prior to entering said mold cavity,
    (h) vent means disposed and structured for the exiting of air from said mold cavity upon the filing of melt therein, said vent means being defined by a plurality of spaces formed between said core pin in the interior surface of the mold cavity, wherein the exterior portion of said core pin extends outwardly from the interior of the mold cavity and engages said interior surface thereof at a plurality of spaced apart points adjacent the location of exiting,
    (i) adjusting means for regulating in-flow imbalance characteristics of the plastic melt between said mold cavity and said core pin, said adjusting means disposed and structured to selectively adjust the relative transverse positions of the core pin and said interior surface of said mold cavity, whereby a preferred alignment between said mold cavity and said core pin can be established.

2. An assembly as in claim 1 wherein said adjustment means comprises a plurality of adjustment screws threadably and movably mounted on said spider element and capable of extending through said spider element into engagement with an exterior surface of said mole cavity, said mole cavity adjustable relative to said spider element and core pin upon movement of said adjustment screws.

3. An assembly as in claim 2 wherein the threadable adjustment of said plurality of adjustment screws causes said mold cavity to be moved in transverse relation to said spider element and said core pin and selective positioning of said interior surface of said mold cavity relative to said core pin.

4. An assembly as in claim 3 wherein said mold cavity is maintained in spaced relation from interior portions of said support member along at least a major portion of the length of said mold cavity.

5. An assembly as in claim 1 wherein said mold cavity fixedly engages said support member and is movable therewith, said adjustment means comprising an adjustment assembly drivingly connected to said support member and capable of selectively moving said support member and mold cavity relative to said core pin.

6. An assembly as in claim 5 wherein said adjustment assembly comprises an automatic, preprogrammable assembly drivingly connected to said support member for regulating the position of said support member and mold cavity relative to said spider element and core pin, whereby inflow imbalance characteristics of the plastic melt into the mold cavity can be regulated by regulating relative positions of said core pin and said interior surface of said mold cavity.

7. An assembly as in claim 1 wherein said exterior peripheral configuration of said core pin is circular and said interior configuration of said mold cavity at said plurality of points of engagement is multi-sided.

8. An assembly as in claim 1 wherein said plurality of apertures are collectively disposed in a substantially circular array and in surrounding relation to said core pin.

9. An assembly as in claim 8 wherein said plurality of apertures define an entrance to said mold cavity, through said open end, for said flow of melt into said mold cavity.

10. An assembly as in claim 1 wherein said deflector pin comprises a substantially conical configuration and is centrally mounted on said spider element externally thereof relative to said mold cavity.

11. An assembly as in claim 1 wherein said vent means comprises said core pin engaging said interior surface of said mold cavity at a plurality of spaced apart points of engagement at a distal end of the tubular product being formed, a plurality of spaces between said points of engagement being dimensioned to allow air to pass therethrough.

12. A molding assembly as in claim 1 wherein said core pin and mold cavity are disposed in an in-line relation to the inflow of melt into said open end of said mold cavity.

* * * * *